United States Patent [19]

Kanojia et al.

[11] 4,061,739

[45] Dec. 6, 1977

[54] ISOLATION OF UTERO-EVACUANT SUBSTANCES FROM PLANT EXTRACTS

[75] Inventors: Ramesh M. Kanojia, Somerville; Seymour D. Levine, North Brunswick, both of N.J.

[73] Assignee: Ortho Pharmaceutical Corporation, Raritan, N.J.

[21] Appl. No.: 703,160

[22] Filed: July 7, 1976

[51] Int. Cl.$^2$ .............................................. A61K 35/78
[52] U.S. Cl. .................................................... 424/195
[58] Field of Search ........................................ 424/195

[56] References Cited

U.S. PATENT DOCUMENTS 3,996,132   12/1976   Mateos et al. ......................... 210/31

*Primary Examiner*—Sam Rosen
*Attorney, Agent, or Firm*—Benjamin F. Lambert

[57] ABSTRACT

A method of obtaining utero-evacuant substances from the zoapatle plant is described. The method involves the isolation and purification of biologically active compounds from the zoapatle plant by chromatography over alumina.

6 Claims, No Drawings

ISOLATION OF UTERO-EVACUANT SUBSTANCES FROM PLANT EXTRACTS

In co-pending application Ser. No. 672,918 filed Apr. 2, 1976, which is a continuation-in-part of application Ser. No. 547,415 filed Feb. 6, 1975, and now abandoned, there is described a method of isolating and purifying extracts of the zoapatle plant which leads to purified material having useful biological activity. The method involves chromatography of the crude material through a column of adsorbent material followed by chromatography through a column of an organic polymeric gel. The present invention relates to a method of isolating and purifying the biologically active materials obtained from the above process by chromatography over alumina.

The zoapatle plant is a bush about 2 m. high that grows wild in Mexico. Botanically it is known as *Montanoa tomentosa* according to Cervantes, Fam. *Compositae*, Tribe *Heliantheae*; another variety of the species is *Montanoa floribunda*. The plant is described in great detail in *Las Plantas Medicinales de Mecico*, third edition, Ediciones Botas (1944).

The plant has been used for centuries in the form of a "tea" or other crude aqueous preparations primarily as a labor inducer or menses inducer for humans. Its use has been documented in the literature, but definitive chemical and pharmacological studies have not been performed.

In the current folk use of the zoapatle plant, the use typically drinks a bitter tasting "tea" brewed from the leaves of the plant by boiling them with water in the same manner used to prepare a hot beverage. She normally does this after having missed a menstrual period and thus is presumably pregnant, although it is known that many frankly pregnant women use the tea to terminate an unwanted pregnancy. The "tea" obviously contains a mixture of complex materials, many of which may be undesirable and unnecessary to produce the desired effect. Natural plant substances are generally known to be exceedingly complex in their composition. Many compounds of similar chemical and physical properties, as well as those with strikingly dissimilar properties, are normally found in these substances and generally present a difficult separation and identification task.

In the above mentioned co-pending application, a method is described for purification of crude extracts from the zoapatle plant which results in a material having biological activity and containing at least three components. This semi-purified material is the starting material for the present invention.

By means of the present invention, two chemically distinct compounds having utero-evacuant properties are obtained by chromatography of the semi-purified material described above on a column of alimina. By utero-evacuant is meant an agent which causes the uterus of warm blooded animals to contract or expel its contents. Such agents are generally employed to induce menses, expel a hydatiform mole, expel or resorb a fetus, induce abortion or delayed labor and in situations in which the contents of the uterus, such as the fetus or placenta, should be evacuated.

The separation of the utero-evacuant substances may be carried out on neutral, basic or acidic alumina. The activity of the alumina may range from I (the most active) to V (the least active). The various activity grades of alumina to be employed are obtained by adding water to alumina of activity I in the proportion of about 3.3% for each lower grade of activity. The preferred adsorbent for the process is acidic alumina of activity IV which is obtained by adding about 10% water to acidic alumnia of activity I.

In carrying out the method of this invention, a sample of the semi-purified utero-evacuant material dissolved in a suitable solvent, such as benzene, toluene, chloroform, diethyl ether, hexane and the like, is added to a column packed with alumina. The column may be prepared dry, but it is preferred to prepare the column in a solvent. The solvent employed is generally the solvent used to dissolve or elute the utero-evacuant material. The column is then eluted with solvent and several fractions are collected. Suitable solvents which can be employed to elute the column include various combinations of polar solvents such as methanol, ethanol, isopropanol, acetone, ethyl acetate, acetonitrile and nitromethane in relatively non-polar solvents such as chloroform, methylene chloride, benzene, toluene, diethyl ether, diisopropyl ether, hexane, cyclohexane and the like. The preferred eluent is one having an increasing gradient of ethyl acetate in cyclohexane. Where, an increased rate of flow is desired, the column can be eluted with the application of low pressure, up to about 10 psi. This can be accomplished through application to the column of an inert gas such as nitrogen, for example. The composition of the fractions is monitored by thin layer chromatography on silver nitrate impregnated silica gel GF plates. The fractions can also be monitored by gas chromatography.

As a result of the above procedure, two chemically distinct compounds having utero-evacuant properties are obtained as evidenced by gas chromatography and spectral analysis.

The utero-evacuant properties of the isolated materials are determined by measuring the extent of uterine contractions and the degree to which pregnancy is interrupted in female animals.

The purified utero-evacuant compounds are effective when administered in doses ranging from 1.0 mg. to about 100 mg./kg. The actual dosage employed will depend upon the species of animal to which the compound is administered. The compounds can be administered in formulations prepared according to acceptable pharmaceutical practices. Suitable formulations would include solutions, suspensions and solid dosage forms.

The following describes the invention in greater particularity and is intended to be a way of illustrating but not limiting the invention.

PREPARATION OF STARTING MATERIAL

Zoapatle leave (10 kg.) and water (30 gallons) are added to a 100 gallon steam-jacketed stainless steel tank. The mixture is heated at 98°–100° C for 2.5 hours with periodic stirring. The hot mixture is filtered through gauze to afford a clear dark tea (about 25 gallons). The solid residue in the tank is washed with hot water (4 gallons), filtered, and the filtrate combined with the tea obtained above. The combined aqueous extracts are extracted with ethyl acetate (30 gallons). The mixture is stirred vigorously and allowed to settle. The top frothy layer is siphoned off to break the emulsion, and as much ethyl acetate separated as possible. Additional ethyl acetate (20 gallons) is added to the mixture and the above process is repeated. The combined ethyl acetate extracts are evaporated at 50° C under vacuum. The residue is extracted with three portions of hot (75°-80°) benzene (10 liters total). The benzene extracts are evaporated at 50° C under vacuum and the residue is washed three times with refluxing hexane (a total of 8 liters). The hexane washed residue is dissolved in acetone (2 liters), Nuchar (10 g.) is added, and the mixture is stirred 1 hour at room temperature. The charcoal is removed by filtration, and the filtrate evaporated by distillation at 30° C under vacuum to afford the crude extract (69 g.).

The crude extract (50 g.) is dissolved in ether (5 l.) and the resulting solution is filtered and washed with saturated sodium bicarbonate solution (500 ml.). The ether is dried over anhydrous sodium sulfate, filtered and concentrated to dryness to afford a light yellow oil (44.6 g.). This oil is then dissolved in chloroform (400 ml.) and the solution added to a column (4 in. × 4 ft.) of 2.5 kg. of neutral sillicic acid packed in chloroform. The column is eluted with chloroform, chloroform-isopropanol mixtures, and 110 fractions are collected. The fractions are evaporated to dryness in vacuo at a temperature below 40° C. The column is eluted as follows:

| Fraction | Volume/Fraction (ml.) | Eluent |
| --- | --- | --- |
| 1-7 | 650 | $CHCl_3$ |
| 8-30 | 500 | isopropanol:$CHCl_3$ (1:41.7) |
| 31-60 | 500 | isopropanol:$CHCl_3$ (1:33.3) |
| 61-105 | 500 | isopropanol:$CHCl_3$ (1:28.6) |
| 106-110 | 500 | isopropanol:$CHCl_3$ (1:25) |

The composition of the fractions is monitored by thin layer chromatography [silica gel, isopropanol-chloroform (1:12.5)] and by gas chromatography — 3% OV17 [methyl silicone:phenyl silicone (1:1) column using a programmed run (150°-250°). Fractions Nos. 78-84 are combined and the solvent removed in vacuo to afford an oily residue of the semi-purified material (5.1 g.) which contains at least three components as indicated by gas chromatography.

EXAMPLE

Sufficient acidic alumina (activity IV) is packed into a galss column (2 in. I.D.) filled with cyclohexane to occupy a height of about 34 in. A solution of the semi-purified material (10 g.) in benzene (25 ml.) is applied to the column of alumina followed by additional benzene (about 15 ml.). The column is eluted first with ethyl acetate:cyclohexane (10:90) and then with an increasing proportion of ethyl acetate in cyclohexane collecting fractions as follows:

| Fraction Number | Fraction Volume | Eluent | Total Volume |
| --- | --- | --- | --- |
| 1-5 | 1000 ml. | 10:90, EtOAc-cyclohexane | 5 l. |
| 6-10 | 1000 ml. | 15:85, EtOAc:cyclohexane | 5 l. |
| 11-15 | 1000 ml. | 20:80, EtOAc:cyclohexane | 5 l. |
| 16-35 | 1000 ml. | 25:75, EtOAc:cyclohexane | 5 l. |
| 36-113 | 250 ml. | 30:70, EtOAc:cyclohexane | ~19.5 l. |

The fractions are monitored by thin layer chromatography on 20% silver nitrate impregnated silica gel GF plates (Analtech) [acetone:benzene, 1:1] and also by gas chromatography on a 3% OV17 [methyl silicone:phenyl silicone, 1:1] column using a programmed run (150°-250°).

Fractions 45-47 are combined and evaporated to give an oil (~280 mg., 2.8%), having the following spectral data: ir (neat) $\mu$: 2.90, 5.96, 6.21; nmr $_{TMS}^{CDCl_3} \delta$: 1.01, 1.13, 1.48, 2.08, 2.11, 3.56, 4.13, 4.25, 5.48 and 6.11.

Fractions 68-98 are combined and evaporated to give an oil (2.18 g., ~22%), having the following spectral data: ir (neat) $\mu$: 2.91 and 5.88; nmr $_{TMS}^{CDCl_3} \delta$: 1.04, 1.15, 1.67, 1.76, 2.18, 3.18, 3.58, 4.15, 4.26, 5.41.

PREPARATION OF ALUMINA - ACTIVITY GRADE IV

Water (150 ml.) is added slowly to acidic alumina (1500 g., Woelm, activity I) with mixing in a 5 l. round bottomed flask. The resulting mixture is mixed thoroughly and uniformly by rotating the flask (on a rotary evaporator) for at least 2 hours. The acidic alumina thus obtained has an acitivity of IV.

The following general procedure is employed to detect uterine contractions in female amimals.

PROCEDURE I

Mature female New Zealand rabbits are anesthetized with sodium pentobarbital and ovariectomized. Following a recovery period of one week, the rabbits are treated with 5 $\mu$g./day s.c. of 17$\beta$-estradiol for 6 consecutive days, followed by treatment with 1.0 mg./day s.c. of progesterone for 7 consecutive days. The uterus and oviducts of the rabbits are perfused 72 hours after the last dose of progesterone according to the method of Heilman et al., (Fertil. Steril. 23:221-229) with slight modifications. The oviduct and uterus are perfused at a rate of 53 $\mu$l./min. The uterus is perfused with a tube extending 1.0 cm. into the lumen of the uterus from the oviducal end. The is ligated at the utero-tubal junction. Another cannula is inserted 1.0 cm. into the uterus through a small incision in the vagina in order to collect perfusate. The material to be tested is administered i.v. through the jugular vein in a vehicle that contains polyethylene glycol 200, polyethylene glycol 400, ethanol and a phosphate buffer. The cannula is attached to a P23-Dc Stathan transducer which in turn is coupled to a Grass Model 5 polygraph and the uterine contractility measured.

Intravenous administration of the compound obtained from Fractions 68-98 is effective in inducing uterine contractions and relaxing the oviduct in 72-hour progesterone withdrawn rabbits in a dose range of 1.0-4.0 mg./kg. The compound obtained for Fractions 45-47 is effective when administered in a dose range of from 25-40 mg./kg.

The following general procedure is employed to detect interruption of pregnancy after implantation has occurred.

PROCEDURE II

Mature, Hartley strain, female guinea pigs are continuously cohabited (monogamously) with males until a vaginal plug (copulation plug) is found in the cage. This time is considered to be day 1 of gestation. Groups of 5-6 females are given test materials intra-peritoneally in the vehicle described in Procedure I on day 22 of gestation. Pigs are sacrificed between the 25th and 45th of gestation and examined for evidence of resorption or abortion.

Intra-peritoneal administration of the material obtained from Fractions 68-98 is effective in interrupting pregnancy when administered in a dose range from 25-85 mg./kg.

What is claimed is:

1. The method of purifying extracts containing utero-evacuant materials obtained from the zoapatle plant which comprises the steps of:

dissolving the mixture of semi-purified utero-evacuant materials in a water-immiscible organic solvent, chromatographing the resultant solution on alumina, eluting the alumina with a mixture of polar and non-polar organic solvents and collecting the fractions containing utero-evacuant materials.

2. The method of claim 1 wherein the zoapatle plant is *Montanoa tomentosa* or *Montanoa floribunda*.

3. The method of claim 1 wherein the waterimmiscible solvent is selected from an aromatic hydrocarbon, a chlorinated hydrocarbon or an aliphatic ether.

4. The method of claim 3 wherein the organic solvent is selected from benzene, chloroform and ether.

5. The method of claim 1 wherein the mixture of polar and non-polar organic solvents comprises a mixture of ethyl acetate:cyclohexane.

6. The method of claim 1 wherein the alumina is acidic alumina of activity IV.

* * * * *

UNITED STATES PATENT AND TRADEMARK OFFICE
CERTIFICATE OF CORRECTION

PATENT NO. : 4,061,739
DATED : December 6, 1977
INVENTOR(S) : Kanojia et al

It is certified that error appears in the above-identified patent and that said Letters Patent are hereby corrected as shown below:

In Column 1, line 31, "use" (2nd Occurrence) should read ---user---
In Column 1, line 57, "alimina" should read ---alumina---
In Column 2, line 29, "this" should read ---thin---
In Column 3, line 44, "galss" should read ---glass---
In Column 4, line 33, "The is ligated" should read
    ---The uterus is ligated---
In Column 4, line 47, "for Fractions" should read
    ---from Fractions---
In Column 4, line 61, "25th and 45th of" should read
    ---25th and 45th day of ---
In Column 6, line 1, Claim 3, "waterimmiscible" should read
    ---water-immiscible---

Signed and Sealed this

Nineteenth Day of September 1978

[SEAL]

Attest:

RUTH C. MASON
Attesting Officer

DONALD W. BANNER
Commissioner of Patents and Trademarks